United States Patent [19]
Ono et al.

[11] Patent Number: 5,908,768
[45] Date of Patent: Jun. 1, 1999

[54] **PROCESS FOR PRODUCING L-GLUTAMIC ACID BY FERMENTATION WITH *E. COLI* RESISTANT TO ASPARTIC ACID ANTIMETABOLITE**

[75] Inventors: Eiji Ono; Nobuharu Tsujimoto; Hiroshi Izui; Kazuhiko Matsui, all of Kawasaki, Japan

[73] Assignee: Ajinomoto Co., Inc., Tokyo, Japan

[21] Appl. No.: 08/844,857

[22] Filed: Apr. 23, 1997

[30] Foreign Application Priority Data

Apr. 23, 1996 [JP] Japan ..................................... 8-100809

[51] Int. Cl.⁶ .............................. C12P 13/14; C12N 1/20
[52] U.S. Cl. ........................ 435/110; 435/252.8; 435/849
[58] Field of Search ................................. 435/110, 252.8, 435/849

[56] References Cited

U.S. PATENT DOCUMENTS 2,947,666  8/1960  Huang ................................. 435/252.33
5,573,945  11/1996 Ono et al. ........................... 435/252.33

FOREIGN PATENT DOCUMENTS 2 680 178  2/1993  France .

OTHER PUBLICATIONS

Spring et al., "L–Asparaginase Genes in *Escherichia coli*: Isolation of Mutants and Characterization of the ansA Gene and its Protein Product", Journal of Bacteriology, Apr. 1986, pp. 135–142.

Reitzer L.J., "Aspartate and Asparagine Biosynthesis", In: "Amino Acids: Biosynthesis and Genetic Regulation", Edited by Herrmann K.M. and Somerville R.L., Addison–Wesley Publishing Company, 1983, pp. 133–145.

*Primary Examiner*—Sandra E. Saucier
*Assistant Examiner*—Vera Afremova
*Attorney, Agent, or Firm*—Oblon, Spivak, McClelland, Maier & Neustadt, P.C.

[57] ABSTRACT

A fermentative process for producing L-glutamic acid efficiently and at low cost is disclosed. Also disclosed are microorganisms having improved ability to produce L-glutamic acid. These microorganisms belong to the genus Escherichia, have resistance to an aspartic acid antimetabolite, and are deficient in α-ketoglutaric acid dehydrogenase activity. The process comprises cultivating one of these microorganisms in a liquid medium, accumulating L-glutamic acid in the culture medium, and collecting L-glutamic acid. In particular, *E. coli* AF13199 (FERM BP-5807).

12 Claims, 2 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO:1:

ACGCGCAAGC GTCGCATCAG G                                               21

(2) INFORMATION FOR SEQ ID NO:2:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO:2:

ATCGGCTACG AATTCAGGCA G                                               21

(2) INFORMATION FOR SEQ ID NO:3:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:3:

CCGGTCGCGG TACCTTCTTC                                                 20

(2) INFORMATION FOR SEQ ID NO:4:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (xi) SEQUENCE DESCRIPTION: SEQ ID NO:4:

CGTAGACCGA ATTCTTCGTA TCGCTT                                         26

PROCESS FOR PRODUCING L-GLUTAMIC ACID BY FERMENTATION WITH *E. COLI* RESISTANT TO ASPARTIC ACID ANTIMETABOLITE

BACKGROUND OF THE INVENTION

1. Field of the Invention

The present invention relates to a microorganism which is used to produce L-glutamic acid by fermentation, and a process for producing L-glutamic acid by fermentation using the microorganism. L-glutamic acid is an amino acid which is important as a seasoning and an ingredient in medicines.

2. Description of the Related Art

L-glutamic acid has been produced thus far by fermentation using mainly so-called glutamic acid-producing microorganisms belonging to the genus Brevibacterium, Corynebacterium or Microbacterium or their mutants (Amino-Acid Fermentation, Gakkai Shuppan Center, pp. 195–215, 1986). With respect to a process for producing L-glutamic acid using other strains, a process using microorganisms belonging to the genus Bacillus, Streptomyces, Penicillium or the like (U.S. Pat. No. 3,220,929) and a process using microorganisms belonging to the genus Pseudomonas, Arthrobacter, Serratia, Candida or the like are known (U.S. Pat. No. 356,387). Production levels of L-glutamic acid have been increased considerably by conventional methods. However, to meet the increasing demand in the future, the development of a process for producing L-glutamic acid more efficiently at lower costs has been desired.

Since *Escherichia coli* has a high growth rate and the genetic analysis thereof has progressed remarkably, there is a possibility that this microorganism may be used as an excellent L-glutamic acid-producing microorganism in the future. However, according to a previous report, the amount of L-glutamic acid accumulated by *Escherichia coli* was as low as 2.3 g/liter (J. Biochem., vol. 50, pp. 164–165, 1961). Nevertheless, it has been recently reported that a mutant which is deficient in or has decreased levels of α-ketoglutaric acid dehydrogenase (hereinafter referred to at times as "α-KGDH") activity produces high levels of glutamic acid (French Patent Laid-Open No. 2,680,178).

SUMMARY OF THE INVENTION

It is an object of the present invention to provide a process for producing L-glutamic acid more efficiently at lower costs by improving the L-glutamic acid-producing ability of microorganisms belonging to the genus Escherichia. The present inventors have assiduously conducted investigations on a process for producing L-glutamic acid using microorganisms belonging to the genus Escherichia, and have consequently found that a microorganism belonging to the genus Escherichia and having an L-glutamic acid-producing ability which conferred resistance to an aspartic acid antimetabolite was improved in its ability to produce L-glutamic acid. This finding has led to the completion of the present invention.

The present invention is described below.

(1) A microorganism which belongs to the genus Escherichia which is resistant to an aspartic acid antimetabolite, and has the ability to produce L-glutamic acid.

(2) The microorganism of the above-mentioned (1) which belongs to the genus Escherichia, which has resistance to an 0 aspartic acid antimetabolite, and which is deficient in or has decreased levels of α-ketoglutaric acid dehydrogenase activity.

(3) The microorganism of the above-mentioned (1) or (2) in which the aspartic acid antimetabolite is aspartic acid β-hydroxamate.

(4) A process for producing L-glutamic acid by fermentation, which comprises cultivating the microorganism of the above-mentioned (1) to (3) in a liquid medium, and accumulating L-glutamic acid in the culture medium, and collecting the same.

DETAILED DESCRIPTION OF THE PREFERRED EMBODIMENTS

Figure 1:
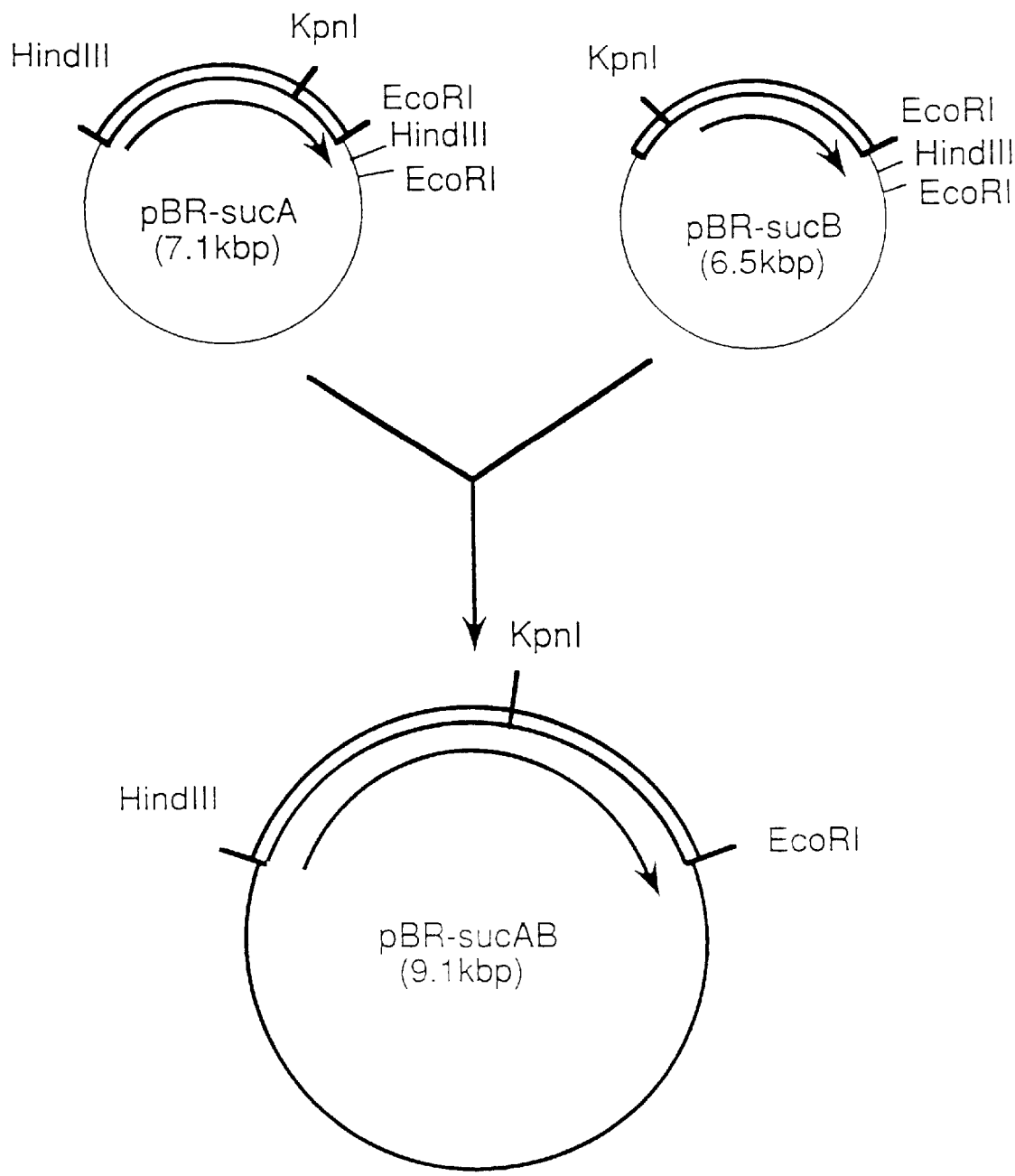
FIG. 1 illustrates construction of pBR-sucAB.

Specific examples of strains belonging to the genus Escherichia which are used in the present invention are as follows.

*Escherichia coli* K-12 (ATCC 10798)
*Escherichia coli* W3110 (ATCC 27325)
*Escherichia coli* B (ATCC 11303)
*Escherichia coli* W (ATCC 9637)

The aspartic acid antimetabolite which is used in the present invention is a substance which inhibits the growth of microorganisms belonging to the genus Escherichia. This growth inhibition is reversed by the addition of L-aspartic acid. Further, the aspartic acid antimetabolite is a substance which suppresses the expression of or inhibits the activity of an enzyme that participates in the biosynthesis of L-aspartic acid. This suppression or inhibition is reversed by the addition of L-aspartic acid.

Examples of the aspartic acid antimetabolite include aspartic acid β-hydroxamate, α-methylaspartic acid, β-methylaspartic acid, cysteine sulfinic acid, difluorosuccinic acid and hadacin. Aspartic acid antimetabolites are commercially available.

The microorganism of the present invention belongs to the genus Escherichia, has resistance to an aspartic acid antimetabolite, and produces L-glutamic acid.

Microorganisms which have other nutritional requirements and are resistant to other antimetabolites also can be used in the present invention so long as they exhibit the above-mentioned properties.

A strain resistant to an aspartic acid antimetabolite may be induced by irradiating the parental strain with ultraviolet rays or treating the same with a mutagen (for example, N-methyl-N'-nitro-N-nitrosoguanidine, hereinafter abbreviated as "NG", and methyl methanesulfonate), and obtaining a strain capable of being grown on an agar medium containing an aspartic acid antimetabolite at a concentration that does not permit growth of the parental strain.

The strain resistant to the aspartic acid antimetabolite is a strain which is more resistant to the aspartic acid antimetabolite than the parental strain.

A microorganism which is deficient in or has decreased levels of α-ketoglutaric acid dehydrogenase activity is taken as an example of the microorganism belonging to the genus Escherichia and having L-glutamic acid-producing ability.

The microorganism which belongs to the genus Escherichia and which is deficient in or has decreased levels of α-ketoglutaric acid dehydrogenase activity, and breeding strategies for the same are described in Japanese Laid-Open Patent Application (Kokai) Nos. 244,970/1993 and 203,980/1995. Specific examples of this microorganism are as follows.

*Escherichia coli* W3110 sucA::Km$^r$

*Escherichia coli* AJ12624 (FERM BP-3853)

*Escherichia coli* AJ12628 (FERM BP-3854)

*Escherichia coli* AJ12949 (FERM BP-4881)

*Escherichia coli* W3110 sucA::Km$^r$ is a strain obtained by disruption of an α-ketoglutaric acid decarboxylase gene of *Escherichia coli* W3110 (hereinafter abbreviated as "sucA gene"); this strain is completely deficient in α-KGDH. W3110 sucA::Km$^r$ is obtained in the following manner.

Primers are synthesized on the basis of the nucleotide sequence of the sucA gene which has been already reported (Eur. J. Biochem., vol. 141, pp. 351–359, 1984), and the sucA gene is amplified by PCR using a chromosomal DNA of *Escherichia coli* W3110 as a template. A drug resistance gene (a kanamycin resistance gene in the present invention) is inserted into the coding region of the sucA gene amplified to construct the sucA gene that has lost its own function. Subsequently, through a homologous recombination, the sucA gene on the chromosome of W3110 is replaced with the sucA gene (sucA::Km$^r$) in which the drug resistance gene has been inserted and which has lost its own function.

The α-KGDH-deficient strain can also be isolated by a conventional mutation method other than the above-mentioned genetic engineering method. For example, the strain is irradiated with X-rays or ultraviolet rays, or is treated with the mutagen such as NG or the like, and the α-KGDH-deficient strain can be selected on the basis of the following properties.

The mutant which is deficient in or has decreased levels of α-KGDH activity cannot grow in a glucose-containing minimum medium, or is able to grow only at a significantly reduced growth rate under aerobic conditions. Nevertheless, when succinic acid or lysine and methionine are added to the minimum medium, normal growth is possible under the same conditions. On the other hand, anaerobic conditions allow the mutant to grow normally in the glucose-containing minimum medium (Molec. Gen. Genetics, vol. 105, pp. 182–190, 1969).

*Escherichia coli* AJ12624 (FERM BP-3853) is a mutant which has a decreased α-KGDH activity and also a reduced ability to degrade L-glutamic acid.

*Escherichia coli* AJ12628 (FERM BP-3854) is a mutant which has a decreased α-KGDH activity and a reduced ability to degrade L-glutamic acid in combination with constitutive expression of the ace operon.

*Escherichia coli* AJ12949 (FERM BP-4881) is a strain obtained by introducing a plasmid containing a phosphoenolpyruvate carboxylase gene and a glutamate dehydrogenase gene into *Escherichia coli* W3110 sucA::Km$^r$.

The above-mentioned mutants which are deficient in or have decreased levels of α-KGDH activity and have a reduced ability to degrade L-glutamic acid in combination with constitutive expression of malate synthase (aceB), isocitrate lyase (aceA) and isocitrate dehydrogenase phosphatase (aceK) operon and/or whose activities of phosphoenolpyruvate carboxylase and glutamate dehydrogenase are amplified are preferable because of the higher level of L-glutamic acid-producing ability.

*Escherichia coli* AJ12624 was listed as deposited at the National Institute of Bioscience and Human Technology of the Agency of Industrial Science and Technology (No. 3, 1-ban, Higashi 1-chome, Tsukuba city, Ibaraki prefecture, Japan, postal code 305) on Jul. 24, 1991, and Deposit No. FERM P-12379 was allotted thereto. This strain was transferred to International Deposition under the Budapest Treaty on May 15, 1992, and Deposit No. FERM BP-3853 was allotted thereto.

*Escherichia coli* AJ12628 was listed as deposited at the National Institute of Bioscience and Human Technology of the Agency of Industrial Science and Technology (No. 3, 1-ban, Higashi 1-chome, Tsukuba city, Ibaraki prefecture, Japan, postal code 305) on Jul. 24, 1991, and Deposit No. FERM P-12380 was allotted thereto. This strain was transferred to International Deposition under the Budapest Treaty on May 15, 1992, and Deposit No. FERM BP-3854 was allotted thereto.

*Escherichia coli* AJ12949 was listed as deposited at the National Institute of Bioscience and Human Technology of the Agency of Industrial Science and Technology (No. 3, 1-ban, Higashi 1-chome, Tsukuba city, Ibaraki prefecture, Japan, postal code 305) on Dec. 28, 1993, and Deposit No. FERM P-14039 was allotted thereto. This strain was transferred to International Deposition under the Budapest Treaty on Nov. 11, 1994, and Deposit No. FERM BP-4881 was allotted thereto.

The microorganism of the present invention belongs to the genus *Escherichia coli* and has resistance to the aspartic acid antimetabolite and the L-glutamic acid productivity. An example of the microorganism of the present invention is *Escherichia coli* AJ13199 (FERM P-15573/FERM BP-5807). *Escherichia coli* AJ13199 is a microorganism obtained by subjecting *Escherichia coli* W3110 sucA::Km$^r$ derived from a non-pathogenic wild strain, *Escherichia coli* W3110 to the conventional mutation. This strain is a mutant which has resistance to aspartic acid β-hydroxamate.

The medium for producing L-glutamic acid in the present invention is a standard culture medium containing carbon sources, nitrogen sources, inorganic salts and, if necessary, organic trace nutrients such as amino acids, vitamins and the like. A synthetic medium and a complete medium are both available. Any carbon source and nitrogen source can be used in the medium so long as a microorganism to be cultured can grow therein.

Examples of the carbon source include glucose, glycerol, fructose, sucrose, maltose, mannose, galactose, starch hydrolysate and molasses; and organic acids such as acetic acid and citric acid. These can be used independently or in combination with other carbon sources.

Examples of the nitrogen source include ammonia; ammonium salts such as ammonium sulfate, ammonium carbonate, ammonium chloride, ammonium phosphate and ammonium acetate; and nitrates.

Examples of organic trace nutrients include amino acids, vitamins, fatty acids, nucleic acids, peptone containing the same, casamino acids, yeast extract and soybean hydrolysate. When cultivating an auxotroph requiring amino acids or the like for its growth, it is necessary to supplement the growth medium with the required nutrients.

Examples of the inorganic salts include phosphoric acid salts, magnesium salts, calcium salts, iron salts and manganese salts.

The cultivation is aerobically conducted at a fermentation temperature of from 20° to 45° C. with a pH of from 5 to 9. When the pH is controlled during the cultivation, neutralization is conducted by adding calcium carbonate or an alkali such as an ammonia gas or the like. When the cultivation is conducted for from 10 hours to 4 days, a considerable amount of L-glutamic acid is accumulated in the culture medium.

L-glutamic acid may be collected from the culture medium after the completion of the cultivation by a known method. For example, L-glutamic acid is collected by a method in which the cells are removed from a culture medium and the residue is then concentrated and crystallized, or through ion-exchange chromatography.

EXAMPLES

The present invention is illustrated more specifically by referring to the following Examples. However, nothing in these examples shall be taken as a limitation upon the overall scope of the invention.

Example 1

Construction of an α-KGDH-deficient strain:

(1) Cloning of the sucA gene and dehydrolipoamido succinyl transferase gene of *Escherichia coli* W3110.

The nucleotide sequences of the sucA gene and dehydrolipoamido succinyl transferase gene (hereinafter abbreviated as "sucB gene") of *Escherichia coli* K12 have been previously reported (Eur. J. Biochem., vol. 141, pp. 351–374, 1984). On the basis of the nucleotide sequences reported, primers represented by Sequence ID No. 1 (5'-ACGCGCAAGCGTCGCATCAGG-3'), Sequence ID No. 2 (5'-ATCGGCTACGAATTCAGGCAG-3'), Sequence ID No. 3 (5'-CCGGTCGCGGTACCTTCTTC-3'), and Sequence ID No. 4 (5'-CGTAGACCGAATTCTTCG TATCGCTT-3') in the Sequence Listing were synthesized, and the sucA gene and the sucB gene were amplified by PCR using the chromosomal DNA of *Escherichia coli* W3110 as a template.

Out of the primers synthesized, the primers used to amplify the sucA gene are represented by Sequence ID Nos. 1 and 2 in the Sequence Listing. Sequence ID No. 1 in the Sequence Listing corresponds to the sequence of from the 45th residue to the 65th residue in the nucleotide sequence of the sucA gene described in Eur. J. Biochem., vol. 141, p. 354, 1984, and Sequence No. 2 in the Sequence Listing corresponds to the sequence of from the 3173rd residue to the 3193rd residue in the nucleotide sequence of the sucB gene described in Eur. J. Biochem., vol. 141, p. 364, 1984.

The primers used to amplify the sucB gene are represented by Sequence ID Nos. 3 and 4 in the sequence list. Sequence ID No. 3 in the Sequence Listing corresponds to the sequence of from the 2179th residue to the 2198th residue in the nucleotide sequence map of the sucA gene described at page 354 of the above-mentioned document, and Sequence No. 4 in the sequence list corresponds to the sequence of from the 4566th residue to the 4591st residue in the nucleotide sequence map of the sucB gene described at page 364 of the above-mentioned document. Incidentally, the sucA gene and the sucB gene form an operon.

The chromosomal DNA which is used as a template when amplifying the sucA gene and the sucB gene by PCR was prepared from *Escherichia coli* W3110 by a standard method (Report on Biological Engineering Experiments, compiled by the Society for Fermentation and Bioengineering, Japan, pp. 97–98, Baifukan, 1992).

PCR was conducted under standard conditions described in PCR Technology (compiled by Henry Ehrlich, Stockton Press, 1989). The resulting PCR products were blunt-ended with a T4 DNA polymerase, and cloned in an EcoRV site of vector pBR322. Plasmid pBR322 having cloned therein the amplified sucA gene was designated as pBR-sucA, and pBR322 having cloned therein the amplified sucB gene was designated as pBR-sucB. Subsequently, upon using these plasmids, *Escherichia coli* JM109 was transformed by a $CaCl_2$ method (Report on Biological Engineering Experiments, compiled by the Society for Fermentation and Bioengineering, Japan, p 139, Baifukan, 1992). Plasmids were prepared from the transformants, and restriction maps of the cloned DNA fragments were constructed. It was confirmed that the cloned genes had the same maps as those of the sucA gene and the sucB gene reported previously.

Subsequently, pBR-sucB was digested with KpnI and EcoRI to prepare a KpnI-EcoRI fragment containing the sucB gene. Meanwhile, pBR-sucA was likewise digested with KpnI and EcoRI to prepare a DNA fragment of a larger size. Both of these fragments were ligated with a T4 DNA ligase to prepare pBR-sucAB as shown in FIG. 1.

(2) Disruption of the sucA gene on the chromosomal DNA of *Escherichia coli* W3110.

Figure 2:
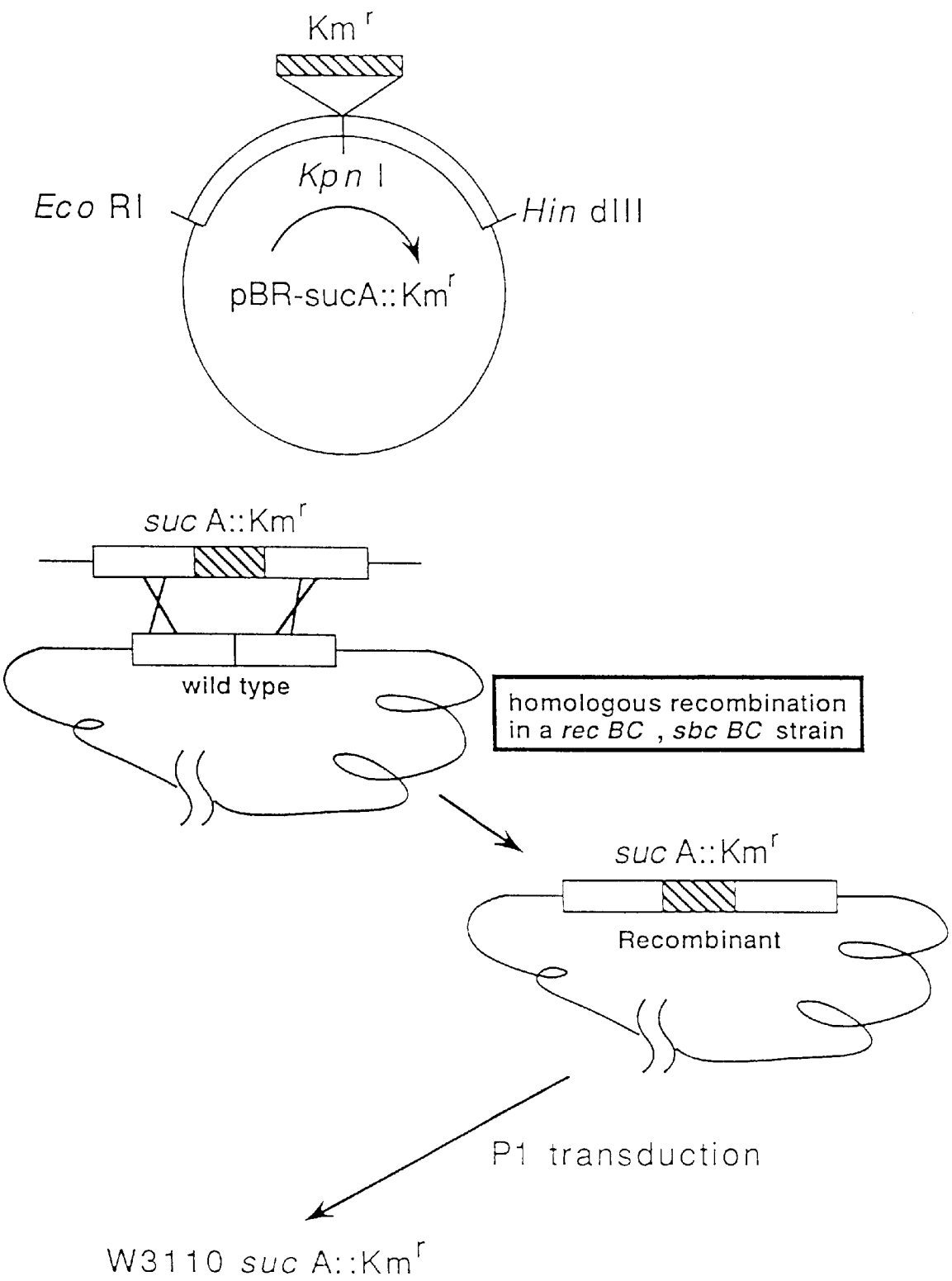
FIG. 2 illustrates the strategy employed in replacing the sucA gene on a chromosomal DNA of *Escherichia coli* W3110 with a sucA gene having inserted therein a kanamycin resistance gene (sucA::Km$^r$).

The flow chart for disruption of the sucA gene on the chromosomal DNA of *Escherichia coli* W3110 is shown in FIG. 2.

First, pBR-sucAB was digested with KpnI, and both terminals thereof were blunt-ended with a T4 DNA polymerase. Meanwhile, pUC4K (purchased from Pharmacia) was digested with PstI to prepare a DNA fragment containing a kanamycin resistance gene. Both terminals thereof were then blunt-ended with a T4 DNA polymerase. These fragments were ligated with a T4 DNA ligase to construct pBR-sucA::Km$^r$. From this plasmid, a HindIII-EcoRI DNA fragment containing the kanamycin resistance gene was prepared. *Escherichia coli* JC7623 strain obtained from *Escherichia coli* Genetic Stock Center (Yale University, U.S.A.) was transformed by a $CaCl_2$ method (Report on Biological Engineering Experiments, the Society for Fermentation and Bioengineering, Japan, p. 139, Baifukan, 1992) using 60 μg of this linear DNA fragment. The strain in which the sucA gene on the chromosomal DNA of JC7623 strain was replaced with the sucA gene having inserted therein the kanamycin resistance gene (sucA::Km$^r$) was selected on an L-agar medium containing 10 g/l of bacto tryptone, 5 g/l of bacto yeast extract, 5 g/l of NaCl (pH 7.2) and 15 g/l of agar containing 25 mg/liter of kanamycin. Since *Escherichia coli* JC7623 strain contains mutations such as recB$^-$, recC$^-$ and sbcB$^-$, homologous recombination can be achieved at a high frequency using a linear DNA. Twelve kanamycin resistant strains were obtained, and chromosomal DNAs were prepared from these twelve strains. Each of the DNAs was digested with KpnI, and southern hybridization was conducted using the DNA fragment containing the sucA gene as a probe. Consequently, it was identified that in all of these twelve strains, the sucA gene thereof was replaced with the sucA gene having inserted therein the kanamycin resistance gene by homologous recombination. This recombination was confirmed as follows. Southern hybridization was conducted using the EcoRI-HindIII fragment of 2.6 kb containing the sucA gene on pBR-sucA as a probe. When the chromosomal DNA of JC7623 strain was digested with KpnI and hybridized with this 2.6 kb fragment, two bands of 5.2 kb and 6.2 kb were detected because the KpnI site was present in the sucA gene. On the other hand, in the strain in which the sucA gene was replaced with the sucA gene having inserted therein the kanamycin resistance gene (1.2 kb), the KpnI site was disrupted when inserting the kanamycin resistance gene into the sucA gene. Accordingly, only one band of 12.6 kb was detected when the KpnI-digested fragment of this chromosomal DNA was hybridized with the 2.6 kb fragment.

The thus-obtained kanamycin-resistant *Escherichia coli* JC7623 strain was infected with P1 phage to prepare a phase lysate, and sucA::Km$^r$ was transduced into *Escherichia coli* W3110 strain. The transduction with P1 phage was conducted by a standard method (Report on Biological Engineering Experiments, the Society for Fermentation and Bioengineering, Japan, pp. 75 76, Baifukan, 1992). The representative strain which was selected as a kanamycin-resistant strain was designated as W3110 sucA::Km$^r$.

The α-KGDH activity of W3110 sucA::Km$^r$ and W3110 strains was measured by the method of Reed et al. (Methods in Enzymology, vol. 13, p. 55, 1969). The results are shown in Table 1. No α-KGDH activity was detected in W3110 sucA::Km$^r$ strain, and it was confirmed that W3110 sucA::Km$^r$ strain was an α-KGDH-deficient-strain.

TABLE 1

|  | W3110 | W3110 sucA::Km$^r$ |
| --- | --- | --- |
| α-KGDH activity | 3.70* | not detected |

*: unit is μmoles/mg protein/min

Example 2

Selection of a strain having resistance to DL-aspartic acid β-hydroxamate:

*Escherichia coli* W3110 sucA::Km$^r$ strain was cultivated in a 2YT liquid medium containing 16 g/l of bacto tryptone, 10 g/l of bacto yeast extract and 5 g/l of NaCl (pH 7.2) at 37° C.

The overnight culture of W3110 sucA::Km$^r$ (0.1 ml) was inoculated in 5 ml of a 2YT liquid medium, and incubated at 37° C. for 3 hours to collect cells in a logarithmic growth phase. The cells were suspended in a 50-mM potassium phosphate buffer (pH 6.0), and the suspension was centrifuged to recollect the cells. The same procedure was conducted again. Subsequently, the cells were suspended in a 50-mM potassium phosphate buffer containing 200 mg/l of NG, and the suspension was allowed to stand for 30 minutes. Then, this suspension was centrifuged to collect the cells. These cells were suspended in a 50-mM phosphate buffer, and the suspension was centrifuged to collect the cells. This procedure was repeated twice, and the cells were washed. Thereafter, the cells were spread on an M9 minimum medium (5 g/l of glucose, 17.1 g/l of disodium hydrogenphosphate-12 hydrate, 3.0 g/l of potassium dihydrogenphosphate, 1.0 g/l of ammonium chloride, 0.5 g/l of NaCl, 0.25 g/l of magnesium sulfate 7-hydrate, 1 mg/l of thiamine hydrochloride and 15 g/l of agar) containing 0.25 g/l of DL-aspartic acid β-hydroxamate and incubated at 37° C. for from 5 to 8 days.

Colonies which were formed on the M9 minimum medium containing 0.25 g/l of DL-aspartic acid β-hydroxamate were picked up, and the individual colonies were purified on the M9 minimum medium through a single colony isolation method. The representative strain having resistance to DL-aspartic acid β-hydroxamate was designed as AJ13199. When W3110 sucA::Km$^r$ was spread on the M9 minimum medium containing 0.25 g/l of DL-aspartic acid β-hydroxamate, it could not grow at all, and no formation of colonies was observed.

Example 3

Cultivation of an L-glutamic acid-producing strain and production of L-glutamic acid:

Each of AJ13199 having resistance to DL-aspartic acid β-hydroxamate and its parental strain W3110 sucA::Km$^r$ which had incubated on an L-agar medium were inoculated into a 500 ml Sakaguchi flask containing 20 ml of the culture medium having the composition noted below, and then cultivated at 37° C. until the sugar in the culture medium was consumed completely. The results are shown in Table 2.

| MEDIUM FOR L-GLUTAMIC ACID PRODUCTION | |
| --- | --- |
| Component | Concentration(g/l) |
| Glucose (sterilized separately) | 40 |
| $(NH_4)_2SO_4$ | 20 |
| $KH_2PO_4$ | 1 |
| $MgSO_4.7H_2O$ (sterilized separately) | 1 |
| $FeSO_4.7H_2O$ | 0.01 |
| $MnSO_4.5H_2O$ | 0.01 |
| Yeast extract | 2 |
| Thiamine hydrochloride | 0.01 |
| $CaCO_3$ (dry-sterilized) | 50 |
| pH 7.0 (adjusted with KOH before autoclaving at 120° C. for 10 min.) | |

TABLE 2

| Strain | OD* | Amount of L-glutamic acid accumulated (g/liter) | Cultivation time (hrs) |
| --- | --- | --- | --- |
| W3110 sucA::Km$^r$ | 0.45 | 19.2 | 25 |
| AJ13199 | 0.76 | 19.8 | 12 |

*: $OD_{562}$ (26-fold dilution)

In AJ13199 having resistance to DL-aspartic acid β-hydroxamate, in comparison to its parental strain, the amount of glutamic acid accumulated was unchanged, but the growth rate was increased, the amount of cells was also increased, the cultivation time was considerably shortened, and the glutamic acid productivity per unit time was greatly improved.

A large number of strains having resistance to DL-aspartic acid β-hydroxamate other than AJ13199 were isolated, and evaluated by the method described in Example 3. In many of these strains, like AJ13199, the growth rate was increased, the amount of the cells was increased, and the cultivation time was considerably shortened.

*Escherichia coli* AJ13199 was listed as deposited at the National Institute of Bioscience and Human Technology of the Agency of Industrial Science and Technology (No. 3, 1-ban, Higashi 1-chome, Tsukuba city, Ibaraki prefecture, Japan, postal code 305) on Apr. 18, 1996, and Deposit No. FERM P-15573 was allotted thereto. This strain was transferred to International Deposition under the Budapest Treaty on Feb. 3, 1997, and Deposit No. FERM BP-5807 was allotted thereto.

This application is based upon Japanese patent Application No. 100809/1996 filed with the Japanese Patent Office on Apr. 23, 1996, the entire contents of which are herein incorporated by reference.

Having now fully described the invention, it will be apparent to one of ordinary skill in the art that many changes and modifications can be made thereto without departing from the spirit or scope of the invention as set forth herein.

---

What is claimed as new and desired to be secured by Letters Patent of the United States is:

1. A process for producing L-glutamic acid, comprising: culturing a microorganism belonging the genus Escherichia which is resistant to an aspartic acid antimetabolite and has the ability to produce glutamic acid in a liquid culture medium, to produce L-glutamic acid in the culture medium, followed by isolating L-glutamic acid from the culture medium.

2. The process of claim 1, wherein the microorganism is deficient in or has decreased levels of α-ketoglutaric acid dehydrogenase activity.

3. The process of claim 2, where the microorganism comprises an inactivated α-ketoglutaric acid decarboxylase gene.

4. The process of claim 1, wherein the aspartic acid antimetabolite is aspartic acid β-hydroxamate.

5. The process of claim 1, wherein the microorganism is a *Escherichia coli* AJ13199 (FERM Accession No. BP-5807).

6. The process of claim 1, wherein the microorganism is *Escherichia coli*.

7. The process of claim 1, wherein the microorganism is resistant to at least one aspartic acid antimetabolite selected from the group consisting of aspartic acid β-hydroxamate, α-methylaspartic acid, β-methylaspartic acid, cysteine sulfonic acid, difluorosuccinic acid and hadacin.

8. The process of claim 1, wherein the microorganism is obtained by irradiating a parent microorganism with ultraviolet rays or treating a parent microorganism with a mutagen, and obtaining a strain capable of being grown on an agar medium containing an aspartic acid antimetabolite at a concentration that does not permit growth of the parent strain.

9. The process of claim 1, wherein the microorganism is cultured at a temperature from 20°–45° C. at a pH from 5–9.

10. The process of claim 9, wherein the microorganism is cultured for a period of time from 10 hours to 4 days.

11. The process of claim 10, wherein the L-glutamic acid is isolated by removing the cells from the culture medium, concentrating the resulting residue and crystallizing the L-glutamic acid.

12. The process of claim 10, wherein the L-glutamic acid is isolated by ion-exchange chromatography.

* * * * *